United States Patent [19]

Geerts et al.

[11] Patent Number: 5,414,180
[45] Date of Patent: May 9, 1995

[54] ORGANO-ALUMINOXY PRODUCT AND USE

[75] Inventors: Rolf L. Geerts, Bartlesville, Okla.; Tara G. Hill, Fairfield, Ohio

[73] Assignee: Phillips Petroleum Company, Bartlesville, Okla.

[21] Appl. No.: 92,143

[22] Filed: Jul. 14, 1993

[51] Int. Cl.$^6$ .................... C07C 2/02; B01J 31/00; C07F 5/02
[52] U.S. Cl. .................... 585/525; 585/511; 585/512; 585/520; 585/522; 585/523; 585/524; 502/103; 502/117; 502/202; 502/351; 556/172; 526/132
[58] Field of Search .............. 556/172, 182, 185; 502/103, 117, 202, 351; 585/502, 511, 512, 520, 522, 523, 524, 525; 526/132

[56] References Cited

U.S. PATENT DOCUMENTS

| | | | |
|---|---|---|---|
| 3,010,989 | 11/1961 | Iloff, Jr. | 260/462 |
| 3,030,406 | 4/1962 | Washburn et al. | 260/462 |
| 3,090,801 | 5/1963 | Washburn et al. | 260/462 |
| 3,092,652 | 6/1963 | Stern et al. | 260/462 |
| 4,808,561 | 2/1989 | Welborn, Jr. | 502/104 |
| 4,897,455 | 1/1990 | Welborn, Jr. | 526/129 |
| 4,925,821 | 5/1990 | Chang | 502/107 |
| 4,937,217 | 6/1990 | Chang | 502/111 |
| 4,952,714 | 8/1990 | Welborn | 556/179 |
| 5,001,244 | 3/1991 | Welborn, Jr. | 556/53 |
| 5,006,500 | 4/1991 | Chang | 502/107 |
| 5,057,475 | 10/1991 | Canich et al. | 502/104 |
| 5,099,050 | 3/1992 | Sangokoya | 556/179 |

FOREIGN PATENT DOCUMENTS

| | | | |
|---|---|---|---|
| 348126 | 6/1989 | European Pat. Off. | C07F 5/06 |
| 0348126 | 12/1989 | European Pat. Off. | |
| 4203753 | 2/1992 | Germany | C08F 4/646 |

OTHER PUBLICATIONS

Chem. Abstracts, vol. 80, No. 16, Apr. 22, 1974, Abstract No. 83953p.
Chem. Abstracts, vol. 107, No. 20, Nov. 16, 1987, Abstract No. 176680p.
*Organometallic Compounds*, G. E. Coates et al., vol. 1, pp. 249-256 (3rd Ed., 1969).

*Primary Examiner*—P. Achutamurthy
*Attorney, Agent, or Firm*—Edward L. Bowman

[57] ABSTRACT

Organic aluminoxy compounds are prepared by reacting an organo boronic acid with a trihydrocarbyl aluminum compound. The resulting products are suitable as components for catalyst systems for the polymerization of olefins.

32 Claims, No Drawings

ORGANO-ALUMINOXY PRODUCT AND USE

The present invention relates to organo-aluminoxy products. The term "organo-aluminoxy" as used herein refers to organic compounds having a multiplicity of groups having the functionality

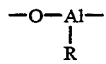

wherein R is a hydrocarbyl radical. In another aspect, the present invention relates to a non-aqueous method for producing aluminoxanes. In still another aspect, the present invention relates to olefin polymerization catalysts prepared using the inventive organo-aluminoxy materials as a cocatalyst. In still another aspect, the present invention relates to a process for polymerizing olefins using such catalyst compositions.

BACKGROUND OF THE INVENTION

Organic aluminoxanes are one form of aluminoxy composition which has been found suitable for use in catalyst systems for polymerizing olefins.

The most common techniques employed commercially for producing aluminoxanes, are believed to involve adding water in predetermined amounts and under controlled conditions to an alkyl aluminum compound. The reaction of water with alkyl aluminums is often a violent reaction and therefore strict process control conditions are generally required when using such a method.

European Published Patent Application No. 348,126 discloses a method for producing hydrocarbyl aluminoxanes by reacting a hydrocarbyl aluminum compound with a trihydrocarbyl boroxine.

In accordance with the present invention, there is provided still another method for preparing aluminoxanes suitable for use as cocatalysts in the polymerization of olefins. In accordance with still another aspect of the present invention, there is provided new aluminoxy products.

In accordance with still yet another object of the present invention, there is provided catalyst systems comprising the aluminoxy composition and a polymerization catalyst.

In yet still another aspect of the invention, there is provided a process for the polymerization of olefins.

SUMMARY OF THE INVENTION

In accordance with the present invention organic aluminoxy compounds are prepared by reacting a trihydrocarbyl aluminum compound with an organic boron compound having boron acid functionality. Also in accordance with the present invention polymerization catalyst systems are prepared using the inventive organic aluminoxy compounds.

DETAILED DESCRIPTION OF THE INVENTION

In accordance with the present invention the inventive organo-aluminoxy compounds are produced by reacting a trihydrocarbyl aluminum compound with an organic boron compound having boron acid functionality under suitable reaction conditions.

It is contemplated that a wide range of trihydrocarbyl aluminum compounds are suitable for use in the present invention. Typically, each hydrocarbyl group would have 1 to 10, more preferably 1 to 8 carbon atoms, each of which could be the same or different. The currently preferred trihydrocarbyl aluminums are trialkyl aluminums. Examples of such alkyl aluminum compounds include trimethyl aluminum, triethyl aluminum, triisobutyl aluminum, and the like. The currently preferred trialkyl aluminum is trimethyl aluminum.

It is further contemplated that a wide variety of organo boron compounds are suitable for the present invention. The term "organic boron compound having boron acid functionality" as used herein refers to organic boron compounds having the following functionality R—B—OH where R is an organo radical. Examples include organo borinic acids and organo boronic acids. Methods for preparing organic boronic acids are disclosed in U.S. Pat. Nos. 3,030,406; 3,090,801; 3,092,652; and 3,010,989, the disclosures of which are incorporated herein by reference. Typically such organo boronic acids can be represented by mono-boronic acids of the formula

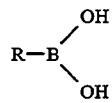

wherein R is an organo radical, typically containing 1 to 20 carbon atoms, more preferably 1 to 8 carbon atoms and diboronic acids of the formula

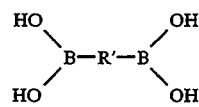

wherein R' is a divalent organic radical having 1 to 20 carbon atoms, more preferably 1 to 8 carbon atoms. Organo borinic acids include compounds of the formula $R_2B(OH)$ wherein R is as defined above.

The organo boron compound and the trihydrocarbyl aluminum compound are reacted in the presence of an organic liquid. Generally a substantially dry liquid would be employed. The term "substantially dry organic liquid" refers to an organic liquid free of any substantial amounts of water, i.e. liquid that is substantially anhydrous. Typical organic liquids would include aliphatic or aromatic liquids such as toluene, benzene, hexane, heptane, isooctane, cyclohexane, methylcyclohexane, decane, and the like. The currently preferred liquids are toluene and heptane.

The reaction conditions employed can vary over a wide range depending upon the particular results desired. Either reactant can be added to the other. Typically, it is desirable to add a solution or suspension of the organic boron compound slowly to a solution of the trihydrocarbyl aluminum. The resulting reaction is exothermic and the addition rate should be controlled for safety. Typically, it is desirable to keep the reaction mixture at a temperature in the range of from about 0° C. to about the boiling point of the organic liquid, generally about 10° C. to about 80° C.

It is generally desirable for the ratio by volume between the dry (substantially anhydrous) organic liquid and the hydrocarbyl aluminum compound to be at least about 4:1 to about 25:1 or even greater.

The molar ratio of the boron compound to the trihydrocarbyl aluminum compound can vary over a wide range depending upon the particular results desired. Typically, the molar ratio of the trihydrocarbyl aluminum compound to the boron acid functionality, i.e. —B—OH, would be in the range of from about 0.5:1 to about 2:1. When the molar ratio of the trihydrocarbyl aluminum to the boron acid functionality is about 0.5 to 1, a very interesting result is noted, namely the production of a solid organo aluminoxy composition containing functionality of the formula

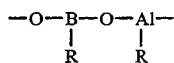

wherein R is a hydrocarbyl group. When the molar ratio of the trihydrocarbyl aluminum to the boron acid functionality is at least 1 to 1, one obtains a product having a formula more generally associated with the term "aluminoxane", namely a composition having repeating units of the formula

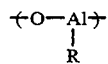

where R is a hydrocarbyl group.

It has generally been noted that the inventive organo aluminoxy products are more active as cocatalysts for transition metal olefin polymerization catalysts if there is also trihydrocarbyl aluminum present. Accordingly, one preferred embodiment involves employing the trihydrocarbyl aluminum compound in such an amount that the molar ratio of the trihydrocarbyl aluminum compound to the boron acid functionality is greater than 1:1, a particularly preferred range would be about 1.05:1 to about 1.75:1. If one uses a molar ratio of trihydrocarbyl aluminum to boron acid functionality of less than 1 to 1 to obtain a solid organo aluminoxy product, the solid can generally be made more active as a cocatalyst by subsequently adding additional trialkyl aluminum to the solid.

Completion of the reaction between the organo boron acid compound and the trihydrocarbyl aluminum is generally indicated by the reduction in the amount of heat being generated by the mixture. Also for many reactants there will be gas evolution while the reaction is continuing.

It is also within the scope of the present invention to prepare the inventive organo-aluminoxy products in the presence of particulate supports, such as for example, particulate silica, alumina, silica-alumina, and the like. One technique involves contacting the particulate support first with one of the reactants and then with the other. Alternatively, the particulate support could be present in a liquid to which one or both of the reactants are added. Another technique involves contacting the support with the solution of organo boron acid compound, then removing the solvent to yield a free-flowing powder. The powder could then be suspended in a suitable liquid. The suspension could then be combined with a solution of the trihydrocarbyl aluminum. After the reaction is complete, the liquid could be removed to yield a solid-containing aluminoxy product. Such solids can be used to form catalyst systems when combined with a suitable olefin polymerization catalyst. In such processes where organo boron acid compound is first contacted with the support, it is generally desired to use a support which is not completely anhydrous so that the boron acid functionality is not deactivated by the support.

In view of the observed activity for the inventive organo aluminoxy products, it is considered that such products will be suitable as replacement for the more conventionally made aluminoxanes in polymerization reactions. Accordingly, the inventive aluminoxane should be suitable as catalyst components with any number of transition metal-containing olefin polymerization catalysts that have been employed in the past with soluble aluminoxanes. Some examples of such transition metal-containing catalysts are disclosed in the previously mentioned U.S. Pat. No. 3,242,099, the disclosure of which is incorporated herein by reference. The use of more than one such catalyst is also within the scope of the present invention. In a preferred embodiment, the catalyst portion of the catalyst system is selected from transition metal compound of metals of Groups IVB, VB, and VIB. Examples of the transition metals thus include zirconium, titanium, hafnium, and vanadium. Such compounds can be represented by the formula $MX_n$ wherein M represents the transition metal atom and X represents a halogen atom or an organo group, and n is the valence state of the transition metal. Some illustrative examples of such transition metal compounds include vanadium dichloride, vanadium trichloride, vanadium tetrachloride, vanadium pentafluoride, vanadium triiodide, titanium dibromide, titanium tetrachloride, titanium trichloride, titanium tetrafluoride, titanium tetraiodide, titanium tetrabromide, zirconium trichloride, zirconium tetrachloride, chromic chloride, titanium tetraethoxide, titanium tetrabutoxide, zirconium tetrabutoxide, tetrabenzyl zirconium, dicyclopentadienyl titanium dichloride, dicyclopentadienyl zirconium dichloride, chromium (III) 2-ethylhexanoate, and the like. It is also within the scope of the invention to prepare a solid catalyst system by contacting a particulate insoluble support with solutions of the inventive aluminoxy product and the transition metal catalyst. Typical supports would include silica, alumina, and the like.

In a particularly preferred embodiment the transition metal catalyst component comprises a metallocene. Examples of metallocenes include compounds of the formula $ML_x$ wherein M is the transition metal, at least one L is aligand coordinated to the transition metal compound having an alkyldienyl skeleton, the other L's can be selected from ligands having alkyldienyl skeletons, hydrocarbon radicals having 1 to 12 carbon atoms, alkoxy radicals having 1 to 12 carbon atoms, aryl oxy radicals having 6 to 12 carbon atoms, halogen, or hydrogen, and x is the valence of the transition metal. Other examples include the hetero-atom containing metallocenes such as disclosed in U.S. Pat. No. 5,057,475.

The term "alkyldienyl skeleton" is intended to include such ligands as cyclopentadienyl, alkyl-substituted cyclopentadienyl compounds such as methyl cyclopentadienyl, ethyl cyclopentadienyl, n-butyl cyclopentadienyl, dimethyl cyclopentadienyl, pentamethyl cyclopentadienyl, and the like. Other examples of such cycloalkyldienyl ligands include substituted and unsubstituted indenyls or fluorenyls, tetrahydroindenyls, and the like. Examples of such metallocenes are disclosed in U.S. Pat. No. 5,091,352, the disclosure of which is incorporated herein by reference. Some specific examples include bis cyclopentadienyl zirconium dichloride, bis(methylcyclopentadienyl) zirconium dichloride, and bis(n-butyl cyclopentadienyl) zirconium dichloride.

It is also within the scope of the present invention to have two of the L groups be cycloalkyldienyl-type groups which are bonded together by a suitable bridging group. Some such metallocenes are referred to herein as sandwich-bonded metallocenes. The term "sandwich-bonded metallocenes" is used herein to indicate that the metal of the metallocene is sandwiched between two opposed cycloalkyldienyl portions of the bridged ligand. Some examples of bridged sandwich bonded metallocenes include 1-(9-fluorenyl)-1-(cyclopentadienyl) methane zirconium dichloride, fluorenyl cyclopentadienyl dimethyl methane zirconium dichloride, 1,2-bis-indenyl ethane hafnium dichloride and the like. Metallocenes also include so-called "half-sandwich-bonded", i.e. those in which only one of two cycloalkyldienyl portions is bonded to the metal. An example would be (1-fluorenyl-1-cyclopentadienyl methane) zirconium trichloride.

It is also within the scope of the present invention to employ the inventive solid aluminoxy product in combination with third generation supported high activity transition metal containing olefin polymerization catalysts. Some examples of typical high activity solid transition metal containing olefin polymerization catalysts include those disclosed in U.S. Pat. Nos. 4,326,988 and 4,394,291, the disclosures of which are incorporated herein by reference.

It is also within the scope of the invention to prepare a prepolymerized solid catalyst composition by combining the transition metal component and a solid form of the inventive aluminoxy composition and conducting prepolymerization of an olefin to produce an active prepolymerized solid which is later used in a polymerization zone.

The particular polymerization conditions employed using the inventive compositions can vary depending upon the particular results desired. Generally the polymerization would be conducted at a temperature in the range of about 0° C. to about 150° C., more typically about 25° C. to about 100° C. It is considered that the inventive solid organo aluminoxy product can be employed in solution, suspension, and gas phase polymerization of a wide range of olefinically unsaturated monomers. The ratio of the transition metal catalyst to the inventive solid aluminoxy product can vary widely depending upon the particular catalyst selected and the results desired. Typically, the atomic ratio of aluminum in the inventive aluminoxy product to the transition metal is in the range of about 1/1 to about 5000/1, preferably about 15/1 to about 1000/1, and more preferably about 100/1 to about 1000/1. For a particular transition metal catalyst it is considered that polymerizations can be carried out under the same conditions as would be suitable for prior art aluminoxanes.

Examples of some monomers for polymerization include ethylene and alpha-olefins having 3 to 20 carbon atoms, such as propylene, 1-butene, 1-hexene, 4-methyl-1-pentene, 1-octene, 1-hexadecene, cyclopentene, norbornene, styrene, 4-methyl styrene, vinyl cyclohexane, butadiene, and the like and mixtures thereof.

Solid forms of the inventive aluminoxy product, whether based on particulate support or on the solid boron-containing aluminoxy product resulting from reaction of the reactants at a low aluminum to boron acid function ratio can be used in slurry type polymerization. A particularly preferred type of slurry polymerization involves the continuous loop reactor type polymerization wherein monomer, feed, catalyst, and diluent, if employed, are continuously added to the reactor as needed and polymer product is continuously or at least periodically removed. Generally in such processes, ethylene is polymerized in the presence of a suitable liquid diluent, a higher alpha-olefin comonomer, and optionally, hydrogen. The polymerization temperature can vary over the range which will allow for slurry polymerization. Often the slurry polymerization would be conducted at a temperature in the range of about 60° C. to about 100° C., although higher and lower temperatures can be used. The employment of hydrogen in such a continuous loop polymerization using the inventive cocatalyst can in some cases affect the molecular weight and/or the molecular weight distribution.

A further understanding of the present invention and its objects and advantages will be provided by referring to the following examples.

EXAMPLE I

A solution of trimethyl aluminum was prepared by adding 4.2 mL of a 2 molar toluene solution of trimethyl aluminum to 5 mL of stirred toluene. Then 0.5 g of methyl boronic acid was added to the rapidly stirred solution in three increments spread out over a one-half hour period. The initial reaction was very vigorous and for that reason the methyl boronic acid was added slowly over the one-half hour period. The mixture was then stirred for 2½ hours and yielded a thick viscous gel. The solids were collected on a filter and dried in a dry box to yield 0.7 grams of solid. A portion of this solid was subjected to elemental analysis by Inductively Coupled Plasma (ICP) analysis. The results indicated that the solid contained about 30.4 wt. % aluminum and 16.7 wt. % boron. This is considered to be similar to what one would have expected for a solid having repeating units of the formula

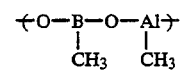

A 0.5 g portion of the solid boron-containing inventive aluminoxy product was suspended in 10 mL of toluene and then 0.011 g of bis(cyclopentadienyl) zirconium dimethyl metallocene was added. The resulting mixture was divided roughly in half. To one-half of the slurry was added 1 mL of the 2 molar toluene solution of trimethyl aluminum. This mixture was then evaluated for the polymerization of ethylene in an autoclave reactor using 2 liters of isobutane and 5.2 mL of the slurry catalyst. The ethylene partial pressure was 250 psig. The two hour polymerization resulted in 67 g of polymer having a melt index of 0.056 and a high load melt index of 1.3

Another polymerization test was conducted using the half of the slurry catalyst mixture that did not have additional trimethyl aluminum added. After two hours of polymerization under the same conditions, only a small trace of polymer was noted. This demonstrates that when one prepares the inventive solid boron-containing aluminoxy cocatalyst, it is necessary to later add additional trihydrocarbyl aluminum in order to obtain significant polymerization activity.

In order to determine whether the polymerization activity was due to the trimethyl aluminum alone, other runs were made employing a metallocene and the trimethyl aluminum without using any organo aluminoxy cocatalyst. The TMA treated inventive organoaluminoxy product was much more active than one would have predicted from the activity of a catalyst using only TMA as cocatalyst.

EXAMPLE II

To a 20 mL toluene solution containing 0.04 moles of trimethyl aluminum was added twenty additional milliliters of toluene and then slowly methyl boronic acid was added in approximately 0.1 g increments. The total amount of methyl boronic acid employed was 0.75 g, i.e. 0.0125 mole. Vigorous gas evolution occurred upon each addition of the acid. The addition was carried out over several hours. A mostly homogeneous solution resulted with some cloudiness.

This material was also subjected to ICP analysis and revealed 22.2 wt. % aluminum and only 1.7 wt. % boron. This is theorized to indicate that the resulting material consists essentially of repeating units of the formula

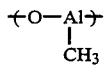

which is analogous to the normal aluminoxanes obtained by reacting trimethyl aluminum with a metal salt hydrate.

An evaluation was then made to determine whether the resulting inventive organic aluminoxy composition was useful as a cocatalyst for a metallocene in the polymerization of ethylene. The catalyst mixture was prepared by adding 0.006 g ($2 \times 10^{-5}$ mole) of bis(cyclopentadienyl) zirconium dichloride to 8.5 mL of the inventive solution so as to yield a catalyst system having an aluminum to zirconium ratio of about 330 to 1. The resulting solution rapidly turned yellow and stayed homogeneous. The ethylene polymerization was carried out in an autoclave for one hour at 250 psi ethylene with 50 psi of hydrogen and produced 347 g of polyethylene which is equivalent to 182,600 g of polyethylene per gram of zirconium per hour. The melt index was too high to measure.

A similar run was carried out without using hydrogen in the polymerization. That run produced 255 g of polyethylene having a melt index of 0.08. The activity was 178,900 g of polyethylene per gram of zirconium per hour. This example demonstrates that when one reacts trimethyl aluminum with methyl boronic acid at a molar ratio of about 3 to 1, i.e. a molar ratio of aluminum to boron acid functionality of 3 to 2, one obtains an organo aluminoxy product that is suitable for use as a cocatalyst with a metallocene.

Another inventive organoaluminoxy composition was prepared by reacting trimethyl aluminum and methyl boronic acid at a molar ratio of about 2.4 to 1, i.e. aluminum to boron acid ratio of 1.2 to 1. In this case, 20 mL of a 2 molar toluene solution of trimethyl aluminum and 20 mL of toluene were added to a flask. To this rapidly stirred solution was slowly added the methyl boronic acid. Vigorous gas evolution occurred upon each addition. Each addition was followed by a period of stirring to ensure complete reaction before the next addition of the methyl boronic acid. The addition of the boronic acid was spread out over a three-day period. The resulting product was a cloudy solution. The solution was filtered and resulted in a clear solution about 0.29 molar in aluminum.

This aluminoxy solution was then evaluated for the polymerization of ethylene. The evaluation was carried out by adding 0.019 g of bis(cyclopentadienyl) zirconium dichloride to a 5 mL portion of the aluminoxy solution. The solution rapidly developed a yellow color and the solution remained homogeneous and turned a deep yellow to orange color over a one to two hour period. The calculated aluminum to zirconium ratio in this catalyst system was about 23 to 1. Then 5 mL of this liquid catalyst system was used to evaluate the polymerization of ethylene, again in an autoclave reactor at an ethylene pressure of 250 psi in the absence of hydrogen. A two hour polymerization resulted in about 15 g of polyethylene.

EXAMPLE III

This example demonstrates the preparation of an inventive aluminoxy composition using a different alkyl boronic acid. In this case 9 mL of toluene was added to a 2 molar toluene solution of trimethyl aluminum. To this rapidly stirred solution was added in small increments n-butyl boronic acid. Vigorous gas evolution was seen. The process resulted in a solution. A 10 mL aliquot of the solution was combined with 0.04 g of bis(cyclopentadienyl) zirconium dichloride to yield a catalyst system having an aluminum to zirconium ratio of about 300 to 1. The catalyst system solution rapidly turned yellow. Then 10 cc of this polymerization catalyst system was employed for the polymerization of ethylene in an autoclave again using 2 liters of isobutane and 250 psig ethylene. The two hour polymerization resulted in 374 g of polyethylene having a melt index of 0.073 and a high load melt index of 3.49.

EXAMPLE IV

In this example, an inventive organic aluminoxy composition is prepared using phenyl boronic acid (also sometimes called benzene boronic acid) rather than an alkyl boronic acid. In this case, 15 mL of toluene was added to 15 mL of a 2 molar toluene solution of trimethyl aluminum. To the rapidly stirred solution was added the phenyl boronic acid. No gas evolution was noted. A total of 1.22 g of the phenyl boronic acid was added over a one-hour period. Then 10 mL of the resulting aluminoxy solution was combined with 29 mg of bis(cyclopentadienyl) zirconium dichloride to yield a catalyst system having an aluminum to zirconium ratio of about 100 to 1. Again, this catalyst system was evaluated for the polymerization of ethylene, in this case using 8.5 mL of the catalyst solution. The polymerization produced 118 g of polyethylene having a melt index of 0.61 and a high load melt index of 27.5 in 15 minutes.

Yet another polymerization test was carried out using the aluminoxy solution produced from phenyl boronic acid. In this case 5 mL of the aluminoxy solution was combined with 7 mg of bis(cyclopentadienyl) zirconium dichloride to yield a catalyst system having an aluminum to zirconium ratio of about 200 to 1. Under the same conditions, it produced 99 g of polyethylene in 40 minutes. The polyethylene had a melt index of 0.12 and a high load melt index of 7.6.

EXAMPLE V

A large batch of an inventive organic aluminoxy composition was prepared by combining 41 mL of a 2 molar toluene solution of trimethyl aluminum with 50 mL of toluene. To this stirred solution was slowly added over a two-day period 1.5 g of methyl boronic acid as a solid. Again, the reaction is vigorous so the additions had to be done slowly and cautiously. Toluene washes were added to wall all of the methyl boronic acid into the trimethyl aluminum solution.

The resulting aluminoxy composition was then evaluated for use in a catalyst system. A 5 mL solution of the inventive aluminoxy composition was combined with 0.1 mL of a 0.005 g per milliliter solution of bis(cyclopentadienyl) zirconium dimethyl to produce a catalyst system having an aluminum to zirconium ratio of 1657. This catalyst system was then evaluated for the polymerization of ethylene at 250 psig ethylene in an autoclave with 2 liters of isobutane. The seventy minute polymerization resulted in 120 g of polyethylene having a high load melt index of 0.83. The productivity of the catalyst was 661,055 g of polyethylene per gram zirconium.

EXAMPLE VI

Another inventive organo aluminoxy composition was prepared using conditions substantially the same as set forth in Example IV, namely the reaction of phenyl boronic acid with trimethyl aluminum wherein the molar ratio of the trimethyl aluminum to the boronic acid was about 3 to 1, i.e. aluminum to boron acid function of about 1.5 to 1. The resulting aluminoxy solution was then combined with bis(cyclopentadienyl)zirconium dichloride to produce a catalyst system having an aluminum to zirconium ratio of about 100 to 1. This was prepared by combining 0.087 g of the metallocene with 30 mL of the inventive aluminoxy solution. This resulting catalyst system was then evaluated for the copolymerization of ethylene and 1-hexene. The polymerizations were conducted again in an autoclave using 2 liters of isobutane. The ethylene pressure was 250 psig and 10 psig of hydrogen was provided from a small vessel.

A first run employed 4 cc of the catalyst system and 50 g of the 1-hexene comonomer and resulted in 160 g of polyethylene copolymer in one hour, polyethylene had a melt index of 67.5.

In a second run, 4 cc of the catalyst system and 125 g of the comonomer was employed and the polymerization resulted in 197 g of polyethylene copolymer in one hour. The polyethylene had a melt index of 27.7.

In still another run, 20 mg of Ti(OC$_2$H$_5$).CH$_3$CH$_3$OH was combined with 10 cc of the catalyst system to result in a mixed catalyst system containing metallocene and non-metallocene catalysts. The resulting solution immediately turned violet or purple.

This mixed catalyst system was then evaluated for the polymerization of ethylene under two different sets of conditions. In both cases, 5 cc of the mixed catalyst system was employed and the reaction was conducted in an autoclave in 2 liters of isobutane.

In one polymerization, ethylene was homopolymerized with 25 psig of hydrogen and 200 psig ethylene. A one-hour polymerization resulted in 151 grams of polyethylene having a Melt Index of 0.87 and a HLMI of 54.6.

In the other polymerization, ethylene was polymerized in the presence of 50 g of 1-hexene. Again 200 psig of ethylene and 25 psig of hydrogen were employed. The one-hour polymerization resulted in 135 grams of polyethylene copolymer having an MI of 5.2 and a HLMI of 226.8.

EXAMPLE VII

To a 10 mL toluene suspension of 0.5 g of methyl boronic acid was added slowly over a one-hour period dropwise by means of a syringe 4.2 mL of a toluene solution of trimethyl aluminum for a total of 0.083 moles of trimethyl aluminum carefully. The initial reaction was quite vigorous. After addition was complete, a cloudy solution resulted which became more heterogeneous as gas evolution ceased. The solution was filtered and the solid collected and dried. The solid was then subjected to C$_{13}$ magic angle spinning NMR analysis. The analysis showed a very broad resonance from +15 to −20 parts per million with two maxima of generally equal intensity at +7 and +2 parts per million.

For comparison, a methyl aluminoxane was prepared using the method disclosed in U.S. Pat. No. 4,808,561, whereby 190 mL of a 2 molar toluene solution of trimethyl aluminum had 3.77 g of Fe(SO$_4$)•7H$_2$O added at room temperature. A slow reaction occurred and the mixture clouded. Then a second addition of 3.77 g of the iron sulfate hydrate was made. The temperature of the reaction increased to 70° C. with considerable gas evolution. Then a third addition of the iron sulfate hydrate was made after the flask had cooled to 40° C. The temperature again jumped to about 58° C. A portion of the resulting methyl aluminoxane solution was stripped of the liquid to result in a solid which was also subjected to the C$_{13}$ magic angle spinning NMR analysis. In this case, there was a sharp peak at 0.81 parts per million and a very broad peak at −7.85 parts per million. The difference between the NMR spectra of the methyl aluminoxane and the solid boron-containing aluminoxy product of the present invention is attributed to the presence of boron heteroatoms in the aluminoxy chain.

EXAMPLE VIII

Another solid boron-containing inventive aluminoxane product was prepared by reacting methyl boronic acid with trimethyl aluminum at a molar ratio of about 1 to 1, i.e. aluminum to boron acid functionality of about 0.5 to 1. In this case, a slurry of 1 g of the methyl boronic acid in 30 mL of toluene had 8.3 mL of a 2 molar toluene solution of trimethyl aluminum added over a 1 ½ hour period. After stirring overnight, a thick viscous slurry resulted. The solids were collected on a filter and dried in a dry box to yield 1.35 grams of solid. These solids were then subjected to laser desorption/Fourier transform mass spectrometry. The mass spectra contained peaks which are considered to reflect fragments of CH$_3$—(Al(CH$_3$)OB(CH$_3$)O)$_n$—Al(CH$_3$)$_2$. The most intense peaks were peaks at about 99 mass in A.M.U. which can be viewed as showing the presence of ions of the formula CH$_3$AlOB(CH$_3$)O+ or (CH$_3$)$_2$AlOB(CH$_3$)+.

That which is claimed is:

1. A process for preparing a hydrocarbyl aluminoxy composition comprising reacting a hydrocarbyl boron compound having boron acid functionality with a trihydrocarbyl aluminum compound under suitable reaction conditions, said hydrocarbyl boron compound being selected from the group consisting of monoboronic acids of the formula

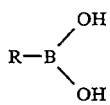

wherein R is a monovalent hydrocarbyl radical, diboronic acids of the formula

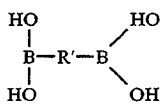

wherein R' is a divalent hydrocarbyl radical, and hydrocarbyl borinic acids of the formula $R_2B(OH)$ wherein each R is a hydrocarbyl radical.

2. A process according to claim 1 wherein each R is a hydrocarbyl radical containing 1–20 carbon atoms and each R' is a hydrocarbyl radical containing 1–20 carbon atoms.

3. A process according to claim 1 wherein said composition comprises a solid product having multiple units of the formula

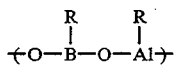

wherein each R is a hydrocarbyl radical having 1 to 10 carbon atoms.

4. A process according to claim 2 wherein each R is a methyl radical.

5. A process according to claim 1 wherein the molar ratio of the trihydrocarbyl aluminum compound to the boron acid functionality is at least about 0.5/1.

6. A process according to claim 5 wherein the molar ratio of the trihydrocarbyl aluminum compound to the boron acid functionality is about 0.5/1.

7. A process according to claim 5 wherein the hydrocarbyl boron compound is selected from the group consisting of alkyl boronic acids in which the alkyl groups have 1 to 4 carbon atoms.

8. A process according to claim 7 wherein the trihydrocarbyl aluminum is selected from the group consisting of trialkyl aluminum compounds in which the alkyl groups have 1 to 4 carbon atoms.

9. A process according to claim 8 wherein said trihydrocarbyl aluminum comprises trimethyl aluminum.

10. A process according to claim 9 wherein the molar ratio of trimethyl aluminum to alkyl boronic acid is about 1 to 1.

11. A process according to claim 9 wherein the molar ratio of the trimethyl aluminum to the alkyl boronic acid is at least about 2 to 1.

12. A process according to claim 11 wherein the molar ratio of the trimethyl aluminum to the alkyl boronic acid is in the range of about 2/1 to about 4/1.

13. A process according to claim 12 wherein the molar ratio of the trimethyl aluminum to the alkyl boronic acid is greater than 2/1.

14. A process according to claim 1 wherein the hydrocarbyl boron compound and the trihydrocarbyl aluminum are reacted in the presence of a particulate inorganic solid.

15. A process according to claim 13 wherein the hydrocarbyl aluminoxy composition produced comprises repeating units of the formula

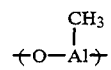

16. A process according to claim 5 wherein the hydrocarbyl aluminoxy product has repeating units of the formula

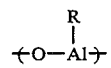

wherein R is a hydrocarbyl radical.

17. A process according to claim 16 wherein said trihydrocarbyl aluminum comprises triethyl aluminum.

18. A process according to claim 17 wherein said boron compound having boron acid functionality comprises methyl boronic acid.

19. A solid boron-containing hydrocarbyl aluminoxy product produced by the process of claim 3.

20. A product of claim 19 wherein each R is a methyl radical.

21. An olefin polymerization catalyst system comprising a hydrocarbyl aluminoxy composition of claim 19 and at least one transition metal-containing olefin polymerization catalyst.

22. A catalyst system according to claim 21 containing at least one transition metal-containing metallocene.

23. A catalyst system according to claim 22 wherein said hydrocarbyl aluminoxy composition is prepared using a molar ratio of the trihydrocarbyl aluminum to the boron acid functionality is less than 1 to 1.

24. A catalyst system according to claim 23 wherein said hydrocarbyl aluminoxy composition is prepared using trimethyl aluminum and methyl boronic acid.

25. A catalyst system according to claim 22 wherein the hydrocarbyl aluminoxy composition is prepared using a molar ratio of the trihydrocarbyl aluminum to the boron acid functionality of less than about 1/1 but at least about 0.5/1.

26. A catalyst system according to claim 25 further comprising trimethyl aluminum.

27. A catalyst system according to claim 26 wherein said hydrocarbyl aluminoxy composition is prepared by reacting trimethyl aluminum with methyl boronic acid.

28. An olefin polymerization process comprising contacting at least one olefin under suitable conditions with a catalyst system of the type set forth in claim 21.

29. A process according to claim 28 wherein said hydrocarbyl aluminoxy composition is prepared by reacting trimethyl aluminum and methylboronic acid.

30. A process according to claim 1 wherein said hydrocarbyl boron compound having boron acid functionality is selected from hydrocarbyl borinic acids, hydrocarbyl boronic acids, and hydrocarbyl diboronic acids in which the hydrocarbyl group contains 1 to 20 carbon atoms.

31. A process according to claim 30 wherein the hydrocarbyl group of the boron compound is aromatic.

32. A process according to claim 31 wherein the hydrocarbyl boron compound is phenyl boronic acid.

* * * * *

UNITED STATES PATENT AND TRADEMARK OFFICE
CERTIFICATE OF CORRECTION

PATENT NO.   : 5,414,180

DATED        : May 9, 1995

INVENTOR(S)  : Rolf L. Geerts and Tara G. Hill

It is certified that error appears in the above-identified patent and that said Letters Patent is hereby corrected as shown below:

Column 11, line 32, please delete "claim 2" and insert therefor ---claim 3---.

Signed and Sealed this

Twenty-second Day of August, 1995

Attest:

BRUCE LEHMAN

*Attesting Officer*     *Commissioner of Patents and Trademarks*